US 6,639,966 B2

(12) United States Patent
Lautenschlager et al.

(10) Patent No.: US 6,639,966 B2
(45) Date of Patent: Oct. 28, 2003

(54) METHOD FOR CHECKING THE PRESENTATION QUALITY OF IMAGING SYSTEMS FOR MEDICAL DIAGNOSTICS WITH RESPECT TO RING ARTIFACTS

(75) Inventors: Markus Lautenschlager, Fürth (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/231,078

(22) Filed: Aug. 30, 2002

(65) Prior Publication Data

US 2003/0063709 A1 Apr. 3, 2003

(30) Foreign Application Priority Data

Aug. 31, 2001 (DE) .......................... 101 42 605

(51) Int. Cl.⁷ ................................. H61B 6/03
(52) U.S. Cl. ........................... 378/15; 378/94
(58) Field of Search .................. 378/4, 8, 15, 901

(56) References Cited

U.S. PATENT DOCUMENTS 5,103,092 A * 4/1992 Takahashi et al. ........ 250/252.1

FOREIGN PATENT DOCUMENTS

DE  31 07 170 A1  9/1982

* cited by examiner

*Primary Examiner*—David V. Bruce
(74) *Attorney, Agent, or Firm*—Harness, Dickey & Pierce, P.L.C.

(57) ABSTRACT

A method is used for checking the presentation quality of imaging systems for medical diagnostics with regard to ring artifacts. The method includes creating at least one test image and defining concentric circles in the test image around a rotational center that is fixed by the imaging system. The method further includes averaging the test image points, arranged along the respective circumferential lines of the circles in circumferential direction of the respective circle in order to create a ring profile in which ring artifacts are detected. Finally, the detected ring artifacts are compared to a pre-selected criterion for evaluating the visual detectability of the detected ring artifacts. The comparison of the detected ring artifacts to the pre-selected criterion is carried out by computing the visual signal noise for each ring artifact and comparing the computed signal noise to the pre-selected criterion.

26 Claims, 4 Drawing Sheets

METHOD FOR CHECKING THE PRESENTATION QUALITY OF IMAGING SYSTEMS FOR MEDICAL DIAGNOSTICS WITH RESPECT TO RING ARTIFACTS

The present application hereby claims priority under 35 U.S.C. §119 on German patent publication number 10142605.4 filed Aug. 31, 2001, the entire contents of which are hereby incorporated herein by reference.

BACKGROUND OF THE INVENTION

Imaging data from an examined test object can be obtained with modern medical diagnostic techniques, for example the computed tomography (CT). As a rule, the test object to be examined is a patient.

The imaging data are generally obtained in digital form and are thus accessible for the digital data processing. Typical operations of the digital data processing are, for example, the intensification, super-imposition or filtering.

In addition to the desired imaging information from the examined test object, the imaging data obtained by use of imaging systems for medical diagnostics normally contain information that can be traced back to interfering influences, such as parasitic induction, during the testing procedure.

In general, the problems are divided into two different categories that reduce the quality of the obtained imaging data: image background noise and artifacts.

In the following, these two problems are to be explained further with the example of the computed tomography.

The image background noise in turn can be divided into several causes.

The main share of the image background noise results from the quantum noise, caused by the fact that each emission of rays is composed of a finite quantum number, so that the quantum number that is measured always fluctuates with normal distribution around an average value.

Further causes for the image background noise are the monochromatic quantum, which are for the most part not exact, of X-ray tubes that can realistically be produced, as well as the scattering of rays based on the interaction between the X-ray radiation used and the electron sheath of atoms during the transmission through the test object.

The artifacts can also be divided further.

Aliasing, partial-volume artifacts, age-hardened artifacts, as well as movement artifacts are typical types of artifacts, the appearance of which in particular depends on the geometry or a movement by the test object.

Effects corresponding to the image background noise, described in the above with the computed tomography, and the artifacts can also be found in other imaging system for medical diagnostics.

Ring artifacts are a special form of the artifacts, caused primarily by the imaging systems themselves that are used for the medical diagnostics.

Imaging systems for medical diagnostics which use (for example in modern computed tomography machines) several detectors (in particular also several detector layers) provide the option of insufficiently calibrating the individual detectors. This is understood to mean that different detectors will measure the same amount of weakening of the rays penetrating the test object differently.

With an insufficient calibration of the individual detectors, for example in a computed tomography machine, the obtained imaging data show concentric rings around the rotational center of the computed tomography machine because of the rotation of the radiation source and the detectors around the test object during the measuring operation. These rings do not have an actual relationship to the test object that is examined. Interferences of this type in the imaging data are called ring artifacts.

Since the manufacturer of an imaging system for medical diagnostics normally calibrates the detectors, the frequency and clarity of ring artifacts is an indicator for the presentation quality of such a system. A low number and low clarity of the ring artifacts indicate great care taken by the manufacturer during the testing and calibration of the imaging system and thus a high quality.

Imaging systems of this type for medical diagnostics are therefore subjected to a final testing by the manufacturer before the system is delivered. Within the framework of this final testing, at least one test image is created for each detector layer with the aid of a test body having a known absorption coefficient (such a test body is also called a "phantom"). As with many other calibration methods, the number of tests performed (test images created) also increases the accuracy. The obtained test images are then checked visually by specially trained personnel for the presence of ring artifacts and the individual detectors are calibrate accordingly.

The disadvantage of this known method, however, is its high cost. Modern CT systems, for example, may require the visual checking of several hundred test images for each system.

German Unexamined Published Patent Application No. 31 07 170 A1 discloses a device for reducing ring-shaped artifacts arranged concentrically around the center of the area to be examined by a computed tomography machine. These artifacts are superimposed on the reconstruction image of the computed tomography machine.

A smoothing device, such as a filter, is proposed for this which smoothes the image values of the reconstruction image in an azimuth direction, relative to the center of the examined area (for example through low-pass filtering). As a result, the ring artifacts are emphasized more in the reconstruction image.

The ring artifacts are subsequently detected in the reconstruction image in a ring-detection stage through filtering along straight lines through the center of the examined area. A median filter, with a filter length that is double the width of the artifacts plus an image point (pixel) is suggested for the filter. By subtracting the image values filtered with the median filter from the smoothed image values, correction image values are computed for all image values.

The computed corrected image values are subsequently compared to a minimum threshold value and a maximum threshold value. On the one hand, this serves to suppress the ring artifacts that cannot be detected visually. On the other hand, it ensures that elements not corresponding to ring artifacts, but some other type of object structure (e.g. a bone structure), are not corrected by mistake.

The disadvantage of the known method and device is that in order to compare the detected ring artifacts to a previously selected criterion, a meridian filtering must first be carried out. Meridian filtering operations of this type are involved computations since they require a sorting function and thus iterative steps. Furthermore, it is necessary to have prior knowledge of the width of the artifacts to determine the filter length.

Furthermore, the correction value used for evaluating the visual detectability of the detected ring artifacts according to German Patent 31 07 170 A1 is a poor indicator for the visual detectability of the detected ring artifacts. This is because it is only an indicator for the expansion of the image values within the filter length and is not a direct indicator of their clarity.

In addition, the meridian filter according to this prior art is used for detecting the ring artifacts as well as for evaluating them. This results in a high dependence on the selected meridian filter as well as the selected filter length. Thus, the result is only meaningful to a limited degree as it relates to the visual detection of the ring artifacts.

SUMMARY OF THE INVENTION

It is the object of an embodiment of the present invention to provide a method and a device for checking the presentation quality of an imaging system for medical diagnostics with respect to ring artifacts, for which the visual detectability of ring artifacts can be evaluated reliably and with little expenditure.

According to an embodiment of the present invention, a method for checking the presentation quality of imaging systems for medical diagnostics with respect to ring artifacts is divided into the following steps:

Creating at least one test image; Defining concentric circles in the at least one test image, wherein the definition of the concentric circles in the at least one test image occurs around a rotational center which is fixed in the test image by the imaging system for medical diagnostics that is used; Averaging the test image points, arranged on the respective circumferential lines of the circles in circumferential direction of the respective circle for creating a ring profile; Detection of ring artifacts in the created ring profile; Comparing the detected ring artifacts to a pre-selected criterion for evaluating a visual detectability of the detected ring artifacts, wherein the detected ring artifacts are compared to the pre-selected criterion by computing the visual signal noise for each ring artifact and comparing the computed signal noise to the pre-selected criterion.

According to an embodiment of the invention, concentric circles must first be defined in the at least one test image before the image points arranged on the circumferential lines of the concentric circles can be averaged. Thus, according to an embodiment of the invention, it is possible to process the imaging data upon which a test image is based in such a way that existing ring artifacts are clearly emphasized based on a reduction of the other image information.

The ring artifacts emphasized in this way are particularly easy to detect and can be evaluated with respect to their visual detectability with the aid of the pre-selected criterion.

For this, an embodiment of the invention suggests comparing the detected ring artifacts with the pre-selected criterion through computing the visual signal noise for each ring artifact and comparing the computed signal noise to the pre-selected criterion.

The visual signal noise of the respective ring artifacts can be computed simply and without great computation expenditure since no iterative steps are required for computing the visual signal noise.

Furthermore, the visual signal noise of the respective ring artifacts is an excellent indicator for the visual detectability of the respective ring artifact since it directly indicates the intensity of each ring artifact.

The criterion to which the computed visual signal noise for evaluating the visual detectability of the ring artifacts is compared represents a measure for evaluating the visual detectability of the detected ring artifacts.

The advantage of using such a criterion is that is allows, for example, an adaptation to the different imaging systems for medical diagnostics or to different test objects used to create the test image.

The method according to an embodiment of the invention thus makes it possible in a particularly simple and reliable manner to evaluate the visual detectability of ring artifacts detected in a test image.

Since the frequency and clarity of ring artifacts in a test image also indicates the presentation quality of an imaging system for medical diagnostics, the quality of such a system can easily be checked with an evaluation of the visual detectability of detected ring artifacts.

For an automatic detection and/or evaluation of ring artifacts in the test image, it is advantageous if a pixel noise that depends on the respective radius of the respective circle is detected at the same time as the ring profile for each circumferential line of the circles is created and if the visual signal noise for each ring artifact is computed with the following formula:

$$SNR = \alpha \cdot \frac{\sum_{r=r\min}^{r\max} R_r B_r^2}{\sqrt{\sum_{r=r\min}^{r\max} R_r B_r^2 S_r^2}}$$

wherein

SNR is the visual signal noise of the respective ring artifact to be computed $\alpha$ is a constant $B_r$ is the ring profile of the test image that is averaged along the respective circumferential lines of the circles, $R_r$ is the radius for the circumferential line of the respective circle, along which the test image is averaged, $S_r$ is the pixel noise depending on the respective radius $R_r$, r is an index that describes with an appropriate grid (scanning grid) the radius $R_r$ and $r_{min}$, $r_{max}$ are the start and end radii of the various detected and potentially visible ring artifacts.

The pixel noise depending on the respective radius of the respective circle can thus preferably be determined during the averaging of the image points arranged on the circumferential line of the respective circle.

The constant $\alpha$ can be equal to 1, but preferably assumes the value $\alpha = \sqrt{2\pi}$ for standardizing the visual signal noise.

It is preferable if the ring profile is subjected to a low-pass filter for noise suppression prior to the detection of the ring artifacts and/or a high-pass filter for suppressing long-wave interferences since ring artifacts in a ring profile processed in this way are even easier to detect.

According to one preferred embodiment, the ring artifacts in the ring profile are detected through a detection of the mathematical sign change in the ring profile.

To check the quality of the image representation in imaging systems for medical diagnostics with the aid of a uniform scale, it is furthermore advantageous if the threshold value for the visual detection of the ring artifacts is determined in another method step and the threshold value is compared to the evaluated visual detectability of the detected ring artifacts.

Determining a threshold value for the visual detectability of the ring artifacts not only permits the evaluation of the visual detectability of the detected ring artifacts with the above-described criterion, but also allows checking the evaluated visual detectability of the detected ring artifacts with respect to the highest permissible value for the visual detectability of the detected and evaluated ring artifacts. This highest permissible value, for example, can depend on the imaging system for medical diagnostics to be checked, or can be predetermined client-specific in the form of specified values.

The threshold value for the signal noise of the respective ring artifact is preferably fixed since the signal noise for all ring artifacts can be computed easily with the aid of the above provided formula.

For one preferred embodiment, the presentation quality of the imaging system for medical diagnostics to be checked is judged to be insufficient if the visual detectability or the signal noise of the respectively detected ring artifacts is higher than the threshold value.

When checking imaging systems for medical diagnostics, it is an advantage based on better standardization if the at least one test image can be created with the aid of a homogenous phantom, meaning with the aid of a test body with known absorption coefficient. This homogeneous phantom can be a water phantom for example.

Another advantage when using a phantom to create the at least one test image is that interfering influences based on the nature of the test object can be avoided, or that these influences occur in the same way for all imaging systems for medical diagnostics that must be checked.

The method according to an embodiment of the invention is particularly good for checking the presentation quality of images created with computed tomography machines since these have a high number of detector layers. As a result, checking the image presentation quality of computed tomography machines by use of a conventional visual evaluation of test images with trained personnel is particularly expensive and involved owing to the high numbers of test images.

According to an embodiment of the invention, a device for realizing the method according to an embodiment of the invention is also provided and comprises the following components:

A defining device for defining concentric circles in the at least one test image created by the imaging system for medical diagnostics to be checked, wherein the definition of the concentric circles in the at least one test image occurs around a rotational center which is fixed in the test image by the imaging system for medical diagnostics used;

An averaging device that is designed to average the image points of the test image, arranged on the respective circumferential lines of the circles, for creating a ring profile in circumferential direction;

A detector that is designed to detect ring artifacts in the created ring profile; and A comparator that is designed to compare the detected ring artifacts for evaluating a visual detectability of the detected ring artifacts to a pre-selected criterion, wherein the comparator is further modified to compute the visual signal noise for each ring artifact and to compare the computed signal noise to the pre-selected criterion.

An embodiment of the present invention also relates to a computer program product that is suitable for realizing the method if loaded into a memory of a processor.

BRIEF DESCRIPTION OF THE DRAWINGS

In the following, exemplary aspects of the invention are explained further with the aid of drawings, which show:

FIGS. 4-1, 4-2, 4-3, 4-4 Schematically the realization of the method according to an embodiment of the invention with the aid of a test image.

DETAILED DESCRIPTION OF THE PREFERRED EMBODIMENTS

A device 10 according to an embodiment of the invention shown in FIG. 1, which is suitable for realizing the method according to an embodiment of the invention, is described in further detail in the following.

The device 10 is connected to an imaging system for medical diagnostics 11, for example a computed tomography machine, and comprises a defining device 12, an averaging device 13, a detector 14, as well as a comparator 15. An output device 16 (for example a monitor, a printer or a signal transmitter) is also connected to the device 10.

The defining device 12 is suitable for defining concentric circles 46 in a test image 41 created by the imaging system 11 for medical diagnostics to be checked. In the process, the center of the concentric circles 46 is specified for the imaging system 11 for medical diagnostics that is used. The center corresponds thus to the rotational center around which a radiation source and detectors for the imaging system 11 for medical diagnostics are moved during a test operation.

The circles 46 function as input variable for the averaging device 13 that is connected to the defining device 12.

The averaging device 13 is suitable for averaging image points, arranged on the respective circumferential lines of the respective circles 46, in the test image 41 that is created by the imaging system 11 for medical diagnostics in order to create a ring profile 42 in circumferential direction of the respective circle 46.

With the aid of the defined circles 46 it is thus determined which image points (pixels) of the test image 41 are to be used for the averaging.

A one-dimensional ring profile is consequently obtained at the output of the averaging device 13. The profile provides a single averaged value for all image points on a respective circle 46 and thus for each respective radial distance of the image points from the center of the concentric circles.

Since the averaging occurs along the circles 46 and thus along the shape of possibly existing ring artifacts 43, 44, the image points of a ring artifact 43, 44 are averaged only with image points of the same ring artifact 43, 44. The ring artifacts 43, 44 as such continue to exist and are assigned a uniform value (average value of the image points of the ring artifact 43, 44).

Image elements 45 of the test image 41, which are not ring artifacts 43, 44, are also averaged with the averaging device 13 along the circles 46. Since the image points of the image elements 45 are therefore averaged with a random selection of image points, in part distributed across the total test image 41, the image element 45 as such is lost. The image points of the image element 45, however, enter into the average value of the respective circle 46, along which the averaging takes place.

The device 10 according to an embodiment of the invention permits an averaging of the test image 41 such that ring artifacts 43, 44 are emphasized, whereas other image elements 45 of the test image 41 are suppressed.

The detector 14 is connected to the averaging device 13 and is suitable for detecting ring artifacts 43, 44 in the generated ring profile 42. Such a detection with the detector 14 is used for distinguishing elements of the ring profile 42, which can be traced back to ring artifacts, and to distinguish these from elements of the ring profile 42 that can be traced back to other image elements 45.

The detector 14 is furthermore connected to the comparator 15 that is suitable for comparing the detected ring artifacts 43, 44 to a pre-selected criterion for evaluating the visual detectability of the detected ring artifacts 43, 44. In the process, the detected ring artifacts are compared to the pre-selected criterion by computing the visual signal noise for each ring artifact 43, 44 and by comparing the computed signal noise to the pre-selected criterion.

Since no iterative steps are required for computing the visual signal noise, the visual signal noise of the respective ring artifacts 43, 44 can be computed easily and without high computing expenditure.

Furthermore, the visual signal noise of the respective ring artifacts 43, 44 is an excellent indicator for the visual detectability of the respective ring artifact 43, 44 since it directly indicates the intensity of the respective ring artifact 43, 44.

The advantage of using a criterion to which the computed visual signal noise is compared is that it permits an adaptation to different imaging system for medical diagnostics or to different test objects during the creation of the test image.

The result of evaluating the visual detectability of the detected ring artifacts 43, 44 is a measure, standardized with the aid of the pre-selected criterion, for the presentation quality of the imaging system 11 for medical diagnostics to be checked. This measure can be output via an output device 16 to a user of the device 10 according to an embodiment of the invention.

Figure 1:
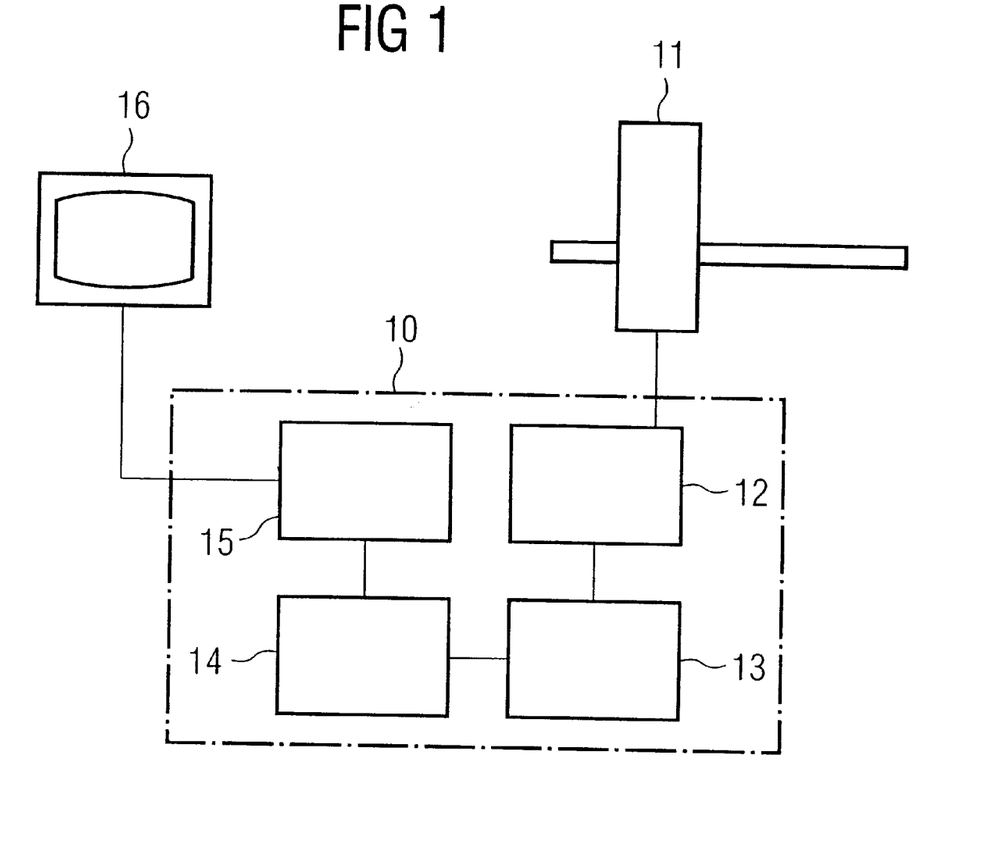
FIG. 1 A device suitable for realizing the method according to an embodiment of the invention.

Alternative to the embodiment shown in FIG. 1, it must be noted that the defining device 12, the averaging device 13, the detector 14 as well as the comparator 15 can form a single unit. For example, they can be jointly realized in a computer chip (not shown herein).

Figure 2:
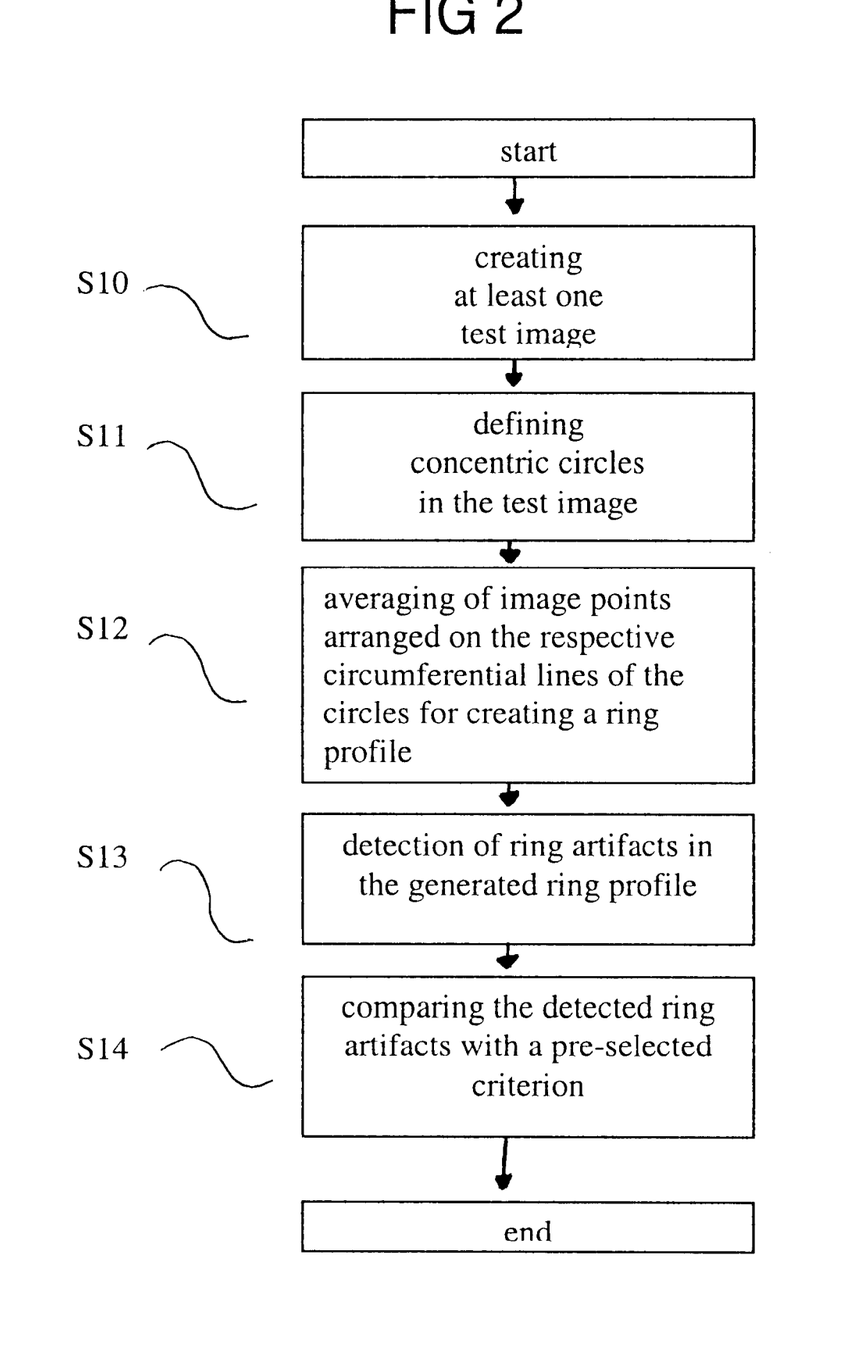
FIG. 2 Schematically the course of the method according to an embodiment of the invention with the aid of a first embodiment.

FIG. 2 shows schematically the course of the method according to an embodiment of the invention, based on a first preferred embodiment, such as can be realized with the above-described inventive device 10 for example.

According to this first preferred embodiment, a test image 41 of a homogeneous water phantom is obtained in a first step S10 by using the imaging system 11 for medical diagnostics (a homogeneous phantom is generally understood to be a test body with known absorption coefficients).

Figure 41:
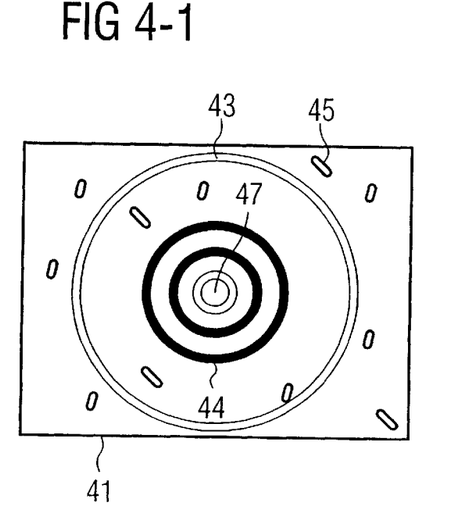

Such a test image 41 of a homogeneous phantom is shown schematically in FIG. 4-1 with the example of a weakening image from a computed tomography machine.

The test image 41 on the whole is an essentially homogeneous image (white area shown in FIG. 4-1) that can be traced back to the homogeneous phantom, with additional and essentially randomly distributed image elements 45 which can be traced back to diverse interference influences. Furthermore, the test image 41 contains ring artifacts 43, 44 that result from an insufficient calibration of detectors for the imaging system 11 for medical diagnostics.

Concentric circles 46 are defined in step S11 in the obtained test image 41 with the aid of the defining device 12.

Figure 42:
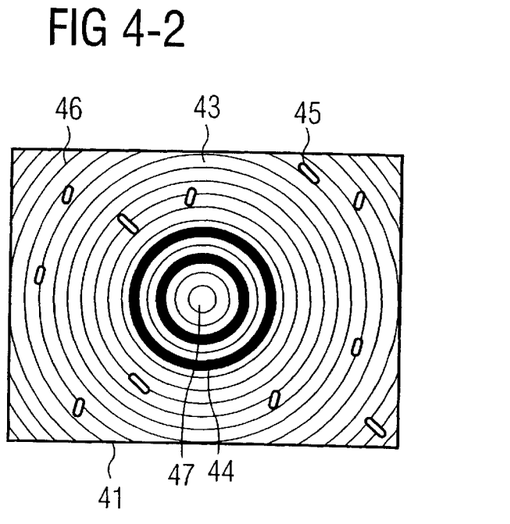

As shown in FIG. 4-2, the definition of the concentric circles 46 in the test image 41 for the embodiment described herein takes place around a rotational center 47 of the test image 41, caused by a movement of the imaging system 11 for medical diagnostics in the test image 41.

In step S12, the image points of the test image 41, arranged along the respective circumferential lines of circles 46, are averaged with the averaging device 13 in circumferential direction of the respective circle 46 in order to generate a ring profile 42. As a result, a (not shown) one-dimensional ring profile is obtained which indicates a single averaged value for all image points on a respective circle 46 and thus for each respective radial distance of the image points from the center of the concentric circles 46.

Figure 43:
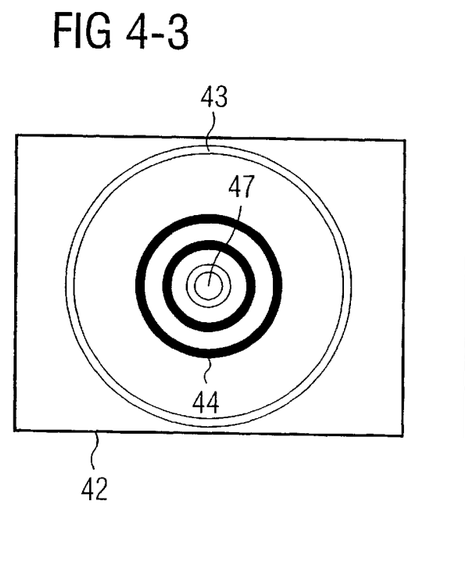

FIG. 4-3 shows a two-dimensional representation of the ring profile 42, obtained through a rotation of the thus generated one-dimensional ring profile around the center of the concentric circles 46.

FIG. 4-3 clearly shows that the image elements 45, resulting from other interferences, no longer exist as such because of the preceding averaging, but are incorporated into the "neutral" image points (white area in the FIG. 4-1) during the averaging because of the dominant number of these points representing the water phantom.

For the embodiment described herein, the ring profile 42 in the following step S13 initially passes through a low-pass filter, not shown herein, for the noise suppression (e.g. three-time filtering of test image 41 with 5-point box car). In order to suppress long-wave interferences, it also passes through a non-depicted high-pass filter (e.g. subtraction of a test image 41 that is filtered three times with a 17 point box car).

The high-pass filter and the low-pass filter are preferably integrated into the averaging device 13. Alternatively, they can also be integrated into the detector 14 or configured as separate components.

Ring artifacts 43, 44 are detected in the generated ring profile 42 in method step S13 and with the aid of the detector 14.

In the embodiment described herein, the ring artifacts 43, 44 are detected by detecting the change in mathematical signs in the ring profile 42.

Figure 44:
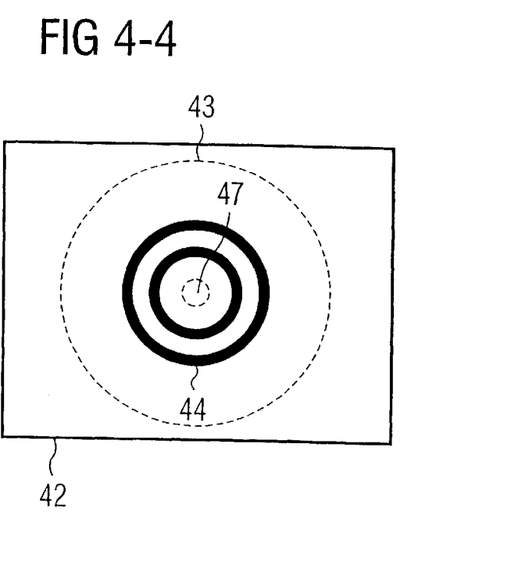

Thus, a ring profile 42 with therein identified ring artifacts 43 and 44 is obtained at the output of the detector 14, as shown with the example in FIG. 4-4.

For this, the respective ring profiles relative to the center of the concentric circles 46 are preferably described with their start and end radii.

In the subsequent step S14, the visual detectability of the detected ring artifacts 43, 44 is evaluated by the comparator 15, meaning it is standardized with the aid of a pre-selected criterion.

For this, the comparator 15 initially computes for each ring artifact 43, 44 the respective visual signal noise.

The comparator 15 then compares the computed signal noise of the respective ring artifacts 43, 44 to the pre-selected criterion, so as to evaluate the visual detectability of the detected ring artifacts 43, 44. The specified criterion can depend, for example on the imaging system for medical diagnostics to be checked or the test object used for creating the test image.

The result of the evaluation through the comparator 15 is a measure for its visual detectability, which is assigned to each detected ring artifact 43, 44.

Thus, the result of the evaluation in step S14 is also a measure for the presentation quality of the imaging system 11 for medical diagnostics to be checked.

In the example shown in FIG. 4-4, the comparator 15 evaluates the ring artifact 43 as being only slightly visually detectable and the ring artifact 44 as clearly visually detectable.

Consequently, the method according to an embodiment of the invention easily and reliably permits the evaluation of the visual detectability of detected ring artifacts without visual evaluation of the test images by specially trained personnel and thus with reduced expenditure.

In addition, this makes it particularly easy to check the presentation quality of imaging systems for medical diagnostics.

Figure 3:
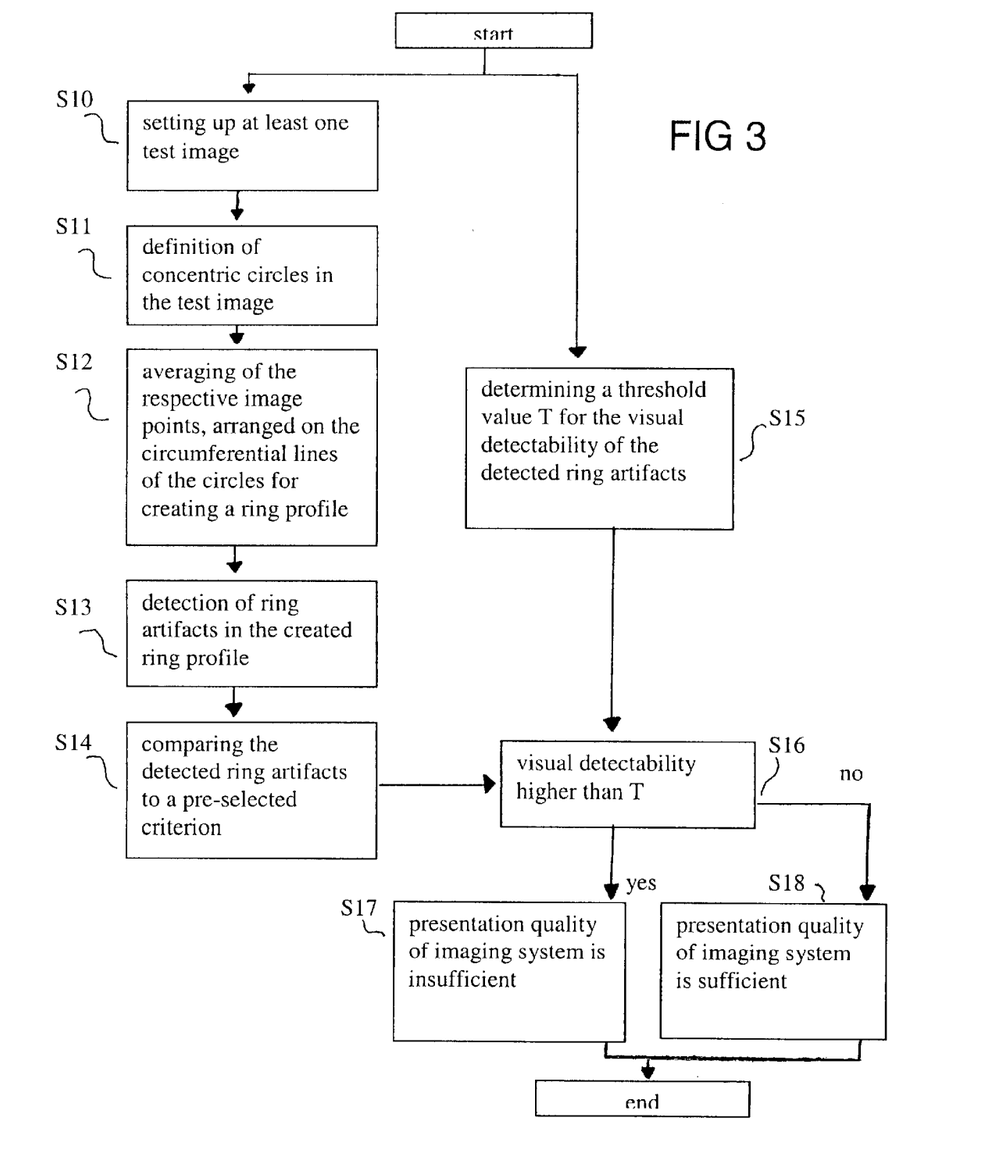
FIG. 3 Schematically the course of the method according to an embodiment of the invention with the aid of a second embodiment.

FIG. 3 schematically shows the course of the method according to an embodiment of the invention in a second preferred embodiment.

It must be taken into consideration here that the second embodiment shown in FIG. 3 is a modified version of the above-explained first embodiment. For that reason, the same method steps are provided with the same reference numbers in the first and second embodiment.

The method described in the second preferred embodiment can also be realized with the device according to an embodiment of the invention shown in FIG. 1.

Analogous to the above-described first embodiment, a test image 41 is initially obtained in step S10 by using the imaging system 11 for medical diagnostics while concentric circles 46 are defined in an additional step S11.

The image points, arranged along the circumferential lines of the circles 46, for the test image 41 are in this case also averaged in method step S12, in circumferential direction of the respective circles 46, in order to generate a ring profile 42.

In addition to averaging of the image points for each circumferential line of the circles 46, a pixel noise $S_r$ is determined in step S12 that depends on the respective radius $R_r$ of the respective circle 46. The index $_r$ here describes the radius $R_r$ with a suitable grid presentation.

As will be explained later on, the pixel noise $s_r$ obtained in this way is used in the embodiment described herein in step S14 for evaluating the visual detectability of the detected ring artifacts 43, 44.

As for the above-described first embodiment, ring artifacts 43, 44 are detected in step S13 in the generated ring profile 42.

These are subsequently evaluated as to their visual detectability in the comparator 15 in step S14 by computing the visual signal noise of the detected ring artifacts 43, 44 and comparing this value to a pre-selected criterion.

In this second, preferred embodiment, the detected ring artifacts 43, 44 are compared to the pre-selected criterion by computing the visual signal noise for each ring artifact 43, 44 and comparing the computed signal noise to the pre-selected criterion, wherein the computation of the visual signal noise for each ring artifact 43, 44 occurs with an evaluation formula, such as the following one:

$$SNR = \alpha \cdot \frac{\sum_{r=rmin}^{rmax} R_r B_r^2}{\sqrt{\sum_{r=rmin}^{rmax} R_r B_r^2 s_r^2}}$$

In this case, SNR stands for the visual signal noise of the respective ring artifact 43, 44 to be computed, $B_r$ stands for the ring profile 42, $R_r$ stands for the radius of the circumferential line for the respective circle 46 along which the text image 41 is averaged, $s_r$ stands for the pixel noise computed in step S12, and $r_{min}$, $r_{max}$ stand for the start and end radii of the different detected ring artifacts 43, 44. The index $_r$ describes the radius $R_r$ with a suitable grid presentation.

Parallel to steps S12 to S14, a threshold value T is fixed in step S15 for the visual detectability of the ring artifacts 43, 44 by use of a threshold value adjustment device that is not shown in FIG. 1 and which can be a component of the device 10 according to an embodiment of the invention.

The threshold value is specified by a user and can depend, for example, on the client's specifications or on the imaging system 11 for medical diagnostics to be checked.

In the following step S16, a test is conducted with the aid of a testing device that is also not shown in FIG. 1 to determine whether the visual detectability evaluated in step S14 of the individually detected ring artifacts 43, 44 is higher than the threshold value T specified in step S15.

The test equipment can also be a component of the device 10 according to an embodiment of the invention, wherein it preferably is integrated into the comparator 15 and is connected to the threshold value adjustment device.

If step S16 results in the value "true" ("yes"), then the presentation quality of the imaging system 11 for medical diagnostics to be checked is evaluated as insufficient, and a corresponding warning is issued via the output device 16 in step S17 to a user of the device 10 according to an embodiment of the invention.

If the step S16 results in the evaluations "false" ("no"), the presentation quality of the imaging system for medical diagnostics to be checked is evaluated as sufficient and the device 10 according to an embodiment of the invention is made available to the user in step S18 via a corresponding release.

Even with the second exemplary embodiment of the device according to an embodiment of the invention, described herein, the visual detectability of detected ring artifacts can be evaluated in a particularly easy and reliable manner and without visual evaluation of the test images by specially trained personnel and thus with reduced expenditure for an evaluation.

With this method, it is furthermore particularly easy to check the presentation quality of imaging systems for medical diagnostics with respect to ring artifacts.

According to another and particularly preferred embodiment of the present invention, the method is implemented into a computer program product which can be loaded into a processor (for example a computer or the above-described inventive device 10) for realizing the method according to an embodiment of the invention.

A computer program product generally is understood to mean that a program in a storage medium is used for realizing the method.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for checking the presentation quality of an imaging system for medical diagnostics with respect to ring artifacts, said method comprising the following steps:

creating at least one test image;

defining concentric circles in the at least one test image, wherein the definition of the concentric circles in the at least one test image occurs around a rotational center which is fixed in the test image by the imaging system for medical diagnostics used;

averaging the test image points, arranged on the respective circumferential lines of the circles in circumferential direction of a respective circle, to generate a ring profile;

detecting ring artifacts in the generated ring profile;

comparing the detected ring artifacts to a pre-selected criterion for evaluating a visual detectability of the detected ring artifacts, wherein the comparison includes computing visual signal noise for each ring artifact and comparing the computed signal noise to the pre-selected criterion.

2. A method according to claim 1, wherein, at the same time as the ring profile is generated, a pixel noise $s_r$ that depends on the respective radius r of the respective circle is determined for each circumferential line of the circles; and wherein the visual signal noise for each ring artifact is computed using an evaluation formula, represented as follows:

$$SNR = \alpha \cdot \frac{\sum_{r=rmin}^{rmax} R_r B_r^2}{\sqrt{\sum_{r=rmin}^{rmax} R_r B_r^2 s_r^2}}$$

wherein

SNR is the visual signal noise of the respective ring artifact to be computed $\alpha$ is a constant $B_r$ is the ring profile of the test image that is averaged along the respective circumferential lines of the circles, $R_r$ is the radius for the circumferential line of the respective circle along which the test image is averaged, $s_r$ is the pixel noise depending on the respective radius $R_r$ of the respective circle, r is an index that describes with an appropriate grid the radius $R_r$ and $r_{min}$, $r_{max}$ are the start and end radii of the various detected ring artifacts.

3. A method according to claim 1, wherein the constant $\alpha$ is equal to $\sqrt{2\pi}$.

4. A method according to claim 1, wherein the ring profile passes through a low-pass filter prior to the detection of the ring artifacts.

5. A method according to claim 1, wherein the ring profile passes through a high-pass filter prior to the detection of the ring artifacts.

6. A method according to claim 1, wherein the ring artifacts are detected by detecting the change in mathematical signs in the ring profile.

7. A method according to claim 1, wherein said method comprises the following additional steps:

determining a threshold value for the visual detectability of the ring artifacts; and comparing the evaluated visual detectability of the detected ring artifacts to the threshold value.

8. A method according to claim 7, wherein the threshold value for the signal noise of the respective ring artifact is fixed.

9. A method according to claim 7, further comprising:

evaluating the presentation quality of the imaging system for medical diagnostics to be checked as insufficient if the visual detectability or the signal noise of the respectively detected ring artifacts is higher than the threshold value.

10. A method according to claim 8, further comprising:

evaluating the presentation quality of the imaging system for medical diagnostics to be checked as insufficient if the visual detectability or the signal noise of the respectively detected ring artifacts is higher than the threshold value.

11. A method according to claim 1, wherein the at least one test image is created with the aid of a homogeneous phantom.

12. A method according to claim 1, wherein the imaging system for medical diagnostics is a computed tomography machine.

13. A method according to claim 2, wherein the constant $\alpha$ is equal to $\sqrt{2\pi}$.

14. A device for realizing the method according to claim 1, said device comprising:

a defining device, designed to define concentric circles in the at least one test image created by the imaging system for medical diagnostics to be checked, wherein the definition of the concentric circles in the at least one test image occurs around a rotational center that is fixed in the test image by the imaging system for medical diagnostics that is used;

an averaging device, designed to average the image points of the test image, which are positioned along the respective circumferential lines of the circles, in order to create a ring profile in circumferential direction of the respective circle;

a detector, designed to detect ring artifacts in the created ring profile; and a comparator, designed to compare the detected ring artifacts to a pre-selected criterion in order to evaluate a visual detectability of the detected ring artifacts, wherein the comparator is further designed to compute the visual signal noise for each ring artifact in order to compare the computed signal noise to the pre-selected criterion.

15. The device of claim 14, wherein the averaging device is further designed to detect for each circumferential line of the circles, a pixel noise that depends on the respective radius of the respective circle at the same time as the ring profile is created, and wherein the comparator is further designed to compute the visual signal noise for each ring artifact with the aid of an evaluation formula, which can be represented as follows:

$$SNR = \alpha \cdot \frac{\sum_{r=rmin}^{rmax} R_r B_r^2}{\sqrt{\sum_{r=rmin}^{rmax} R_r B_r^2 s_r^2}}$$

wherein

SNR is the visual signal noise of the respective ring artifact to be computed $\alpha$ is a constant $B_r$ is the ring profile of the test image that is averaged along the respective circumferential lines for the circles, $R_r$ is the radius for the circumferential line of the respective circle along which the test image is averaged, $s_r$ is the pixel noise depending on the respective radius $R_r$, of the respective circle, r is an index that describes with an appropriate grid the radius $R_r$ and $r_{min}$, $r_{max}$ are the start and end radii of the various detected ring artifacts.

16. A computer program product, suitable for realizing a method according to claim 1 when loaded into a memory of a processor.

17. A method for checking quality of an imaging system for medical diagnostics with respect to ring artifacts, said method comprising the following steps:

creating at least one test image;

defining concentric circles in the at least one test image;

generating a ring profile from the defined concentric circle;

detecting ring artifacts in the generated ring profile; and computing visual signal noise for each ring artifact and comparing the computed signal noise to a pre-selected criterion for evaluating a visual detectability of the detected ring artifacts.

18. The method according to claim 17, wherein the ring profile is generated by averaging test image points, arranged on respective circumferential lines of the circles in a circumferential direction of a respective circle.

19. The method according to claim 17, further comprising:

subjecting the generated ring profile to a low-pass filter for noise suppression prior to the detection of the ring artifacts.

20. The method according to claim 17, further comprising:

subjecting the generated ring profile to a high-pass filter for suppressing long-wave interferences prior to the detection of the ring artifacts.

21. A computer program product, suitable for realizing a method according to claim 17 when loaded into a memory of a processor.

22. A device for checking quality of an imaging system for medical diagnostics with respect to ring artifacts, comprising:

a defining device, designed to define concentric circles in at least one test image created by the imaging system;

an averaging device, designed to average the image points of the test image in order to create a ring profile;

a detector, designed to detect ring artifacts in the created ring profile; and a comparator, designed to compare the detected ring artifacts to a pre-selected criterion in order to evaluate a visual detectability of the detected ring artifacts, wherein the comparator is further designed to compute the visual signal noise for each ring artifact in order to compare the computed signal noise to the pre-selected criterion.

23. The device of claim 22, wherein the definition of the concentric circles in the at least one test image occurs around a rotational center that is fixed in the test image by the imaging system for medical diagnostics that is used.

24. The device of claim 22, wherein the image points of the test image are positioned along the respective circumferential lines of the circles.

25. The device of claim 22, further comprising a low-pass filter, designed to suppress noise in the generated ring profile prior to the detection of the ring artifacts.

26. The device of claim 22, further comprising a high-pass filter, designed to suppress long-wave interferences in the generated ring profile prior to the detection of the ring artifacts.

* * * * *